US008578529B2

(12) United States Patent
Miyano et al.

(10) Patent No.: US 8,578,529 B2
(45) Date of Patent: Nov. 12, 2013

(54) BED FOR MEDICAL IMAGE SCANNING APPARATUS

(75) Inventors: Iwao Miyano, Tokyo (JP); Kenya Sakanaka, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 124 days.

(21) Appl. No.: 13/263,880

(22) PCT Filed: Apr. 21, 2010

(86) PCT No.: PCT/JP2010/057054
§ 371 (c)(1),
(2), (4) Date: Oct. 11, 2011

(87) PCT Pub. No.: WO2010/123024
PCT Pub. Date: Oct. 28, 2010

(65) Prior Publication Data
US 2012/0023671 A1   Feb. 2, 2012

(30) Foreign Application Priority Data
Apr. 22, 2009   (JP) .................... 2009-103802

(51) Int. Cl.
*A47B 13/00*   (2006.01)
(52) U.S. Cl.
USPC .................................. 5/601; 5/611
(58) Field of Classification Search
USPC ............... 5/601, 611, 943, 81.1 HS; 378/209
See application file for complete search history.

(56) References Cited

U.S. PATENT DOCUMENTS

| 4,771,785 A * | 9/1988 | Duer ........................ 600/415 |
| 4,927,127 A * | 5/1990 | Lock ......................... 5/611 |
| 4,984,774 A * | 1/1991 | Zupancic et al. ........... 5/601 |
| 2005/0129181 A1* | 6/2005 | Shinoda ................... 378/209 |
| 2007/0251008 A1* | 11/2007 | Li ............................. 5/601 |
| 2008/0235873 A1* | 10/2008 | Farooqui ..................... 5/601 |

FOREIGN PATENT DOCUMENTS

| JP | 2006-110097 | 4/2006 |
| JP | 2008237911 | 10/2008 |

OTHER PUBLICATIONS

International Search Report in PCT/JP2010/057054.

* cited by examiner

*Primary Examiner* — Robert G Santos
*Assistant Examiner* — Richard G Davis
(74) *Attorney, Agent, or Firm* — Cooper & Dunham LLP

(57) ABSTRACT

An object of the present invention is to provide a bed for a medical image scanning apparatus including a lateral movement device which is light and has less deformation while suppressing a bed height in the lowest position of a top board. A bed for a medical image scanning apparatus includes a base 8, an upper portion frame 2 that supports a top board 1, and a lifting and lowering device 40 that is positioned between the base 8 and the upper portion frame 2 and lifts and lowers the upper portion frame 2, and the lifting and lowering device 40 includes a lateral movement device (a motor 10, a pinion gear 12, and rack 23) which relatively moves at least two members (a rail receiving block 17 and a rotation axis 18, and a rail receiving block 15 and a rotation axis 20) constituting the lifting and lowering device 40 along a direction perpendicular to a longitudinal direction of the upper portion frame 2 in the top board surface of the top board.

11 Claims, 15 Drawing Sheets

BED FOR MEDICAL IMAGE SCANNING APPARATUS

FIELD OF THE INVENTION

The present invention relates to a bed for a medical image scanning apparatus, and particularly, to a bed for a medical image scanning apparatus capable of easily performing an adjusting operation of a photographing view of an object which is disposed on a top board.

DESCRIPTION OF RELATED ART

When performing a CT photographing through an X-ray CT apparatus, since the photographing is performed with a body axis of an object in the center, a wide range of photographing is necessary in order to photograph internal organs such as heart which is deviated from the center of the body axis. As a result, the exposure dose is increased. Then, as one of methods for decreasing the exposure dose in a region other than an object to be photographed, in order to position the object to be photographed, which is at the position deviated from the center of the body axis of the object, to the center of an irradiation X-ray range, a bed for an X-ray CT apparatus having a lateral movement device which moves a top board to a direction perpendicular to the direction of the body axis is suggested.

For example, a bed for an X-ray CT apparatus of Patent Document 1 is constituted by using a driving mechanism in plural steps, in which the driving mechanism includes an upper portion frame which longitudinally moves a top board disposing an object, a lower portion frame in which a mechanism for longitudinally moving the upper portion frame is installed between the upper portion frame and the lowest base for lifting and lowering the upper portion frame, and a center portion base which is installed in a center portion for laterally moving the lower portion frame. According to the configuration, the lower portion frame is laterally moved in the center portion base, the upper portion frame is longitudinally moved in the lower portion frame, a top board is further longitudinally moved by the upper portion frame, the center portion base is lifted and lowered in the lowest base, and an object is transported into an opening of a gantry.

PRIOR ART DOCUMENT

Patent Document

[Patent Document 1] JP-A-6-54842

However, in the Patent Document 1, the center portion base and the lower portion frame for the lateral movement is installed on the lifting and lowering mechanism, the upper portion frame for performing the longitudinal movement is stacked thereon, and the configuration becomes a multilayered structure. Therefore, weight is increased due to the increase of parts other than the frames. In addition, since height of the bed in the lowest position in the multilayered structure is higher compared to that of an apparatus without having the multilayered structure, it is inconvenient when a movement-impaired object is disposed on the top board. In addition, there are numerous operating portions or intermediate supporting members, and there is a problem in that amount of displacement in the portion of the top board is increased due to concentration of deformation in each portion.

The present invention is made in consideration of the above-described problems. An object of the present invention is to provide a bed for a medical image scanning apparatus including a lateral movement device which is light and has less deformation while suppressing the increase of a bed height in the lowest position of a top board.

BRIEF SUMMARY OF THE INVENTION

In order to achieve the above object, in a bed for a medical image scanning apparatus according to the present invention, a lifting and lowering device itself also serves as a lateral movement device. That is, the members constituting the lifting and lowering device include the lateral movement device. Specifically, a bed for a medical image scanning apparatus according to the present invention includes a base, an upper portion frame that supports a top board, and a lifting and lowering device that is positioned between the base and the upper portion frame and lifts and lowers the upper portion frame, in which the lifting and lowering device includes a lateral movement device which relatively moves at least two members constituting the lifting and lowering device along a lateral direction which is a direction perpendicular to a longitudinal direction of the upper portion frame in the top board surface of the top board.

In addition, in the bed for a medical image scanning apparatus according to the present invention, a longitudinal movement device itself may also serve as the lateral movement device. That is, the members constituting the longitudinal movement device may include the lateral movement device. Specifically, a bed for a medical image scanning apparatus according to the present invention includes a base, an upper portion frame that supports a top board, and a longitudinal movement device that is positioned between the base and the upper portion frame and moves the upper portion frame along the longitudinal direction, in which the longitudinal movement device includes a lateral movement device which relatively moves at least one member constituting the longitudinal movement device with respect to the base along a lateral direction which is a direction perpendicular to a longitudinal direction of the upper portion frame in the top board surface of the top board.

According to the present invention, since components of the lifting and lowering device or the longitudinal movement device and components of the lateral movement device are used in common, the lateral movement device can be added to the bed for a medical image scanning apparatus without having an intermediate frame between the base and the upper portion frame. Thereby, the bed for a medical image scanning apparatus including the lateral movement device which is light and has less deformation while suppressing the bed height in the lowest position of the top board can be provided.

DETAILED DESCRIPTION OF THE INVENTION

Hereinafter, embodiments to which the present invention is applied will be described. In addition, hereinafter, in all drawings for explaining the embodiments of the present invention, portions having the same functions are denoted by the same reference numbers, and the repeated descriptions are omitted.

<<First Embodiment>>

A first embodiment is an example that uses a bed for a medical image scanning apparatus (hereinafter, referred to as a "bed") in which the present invention is applied to an X-ray CT apparatus. In the first embodiment, a pantographic arm is used as a lifting and lowering device for the bed, and components of the pantographic arm are used in common for a longitudinal movement device and a lateral movement device.

(Overall Configuration)

Figure 1:
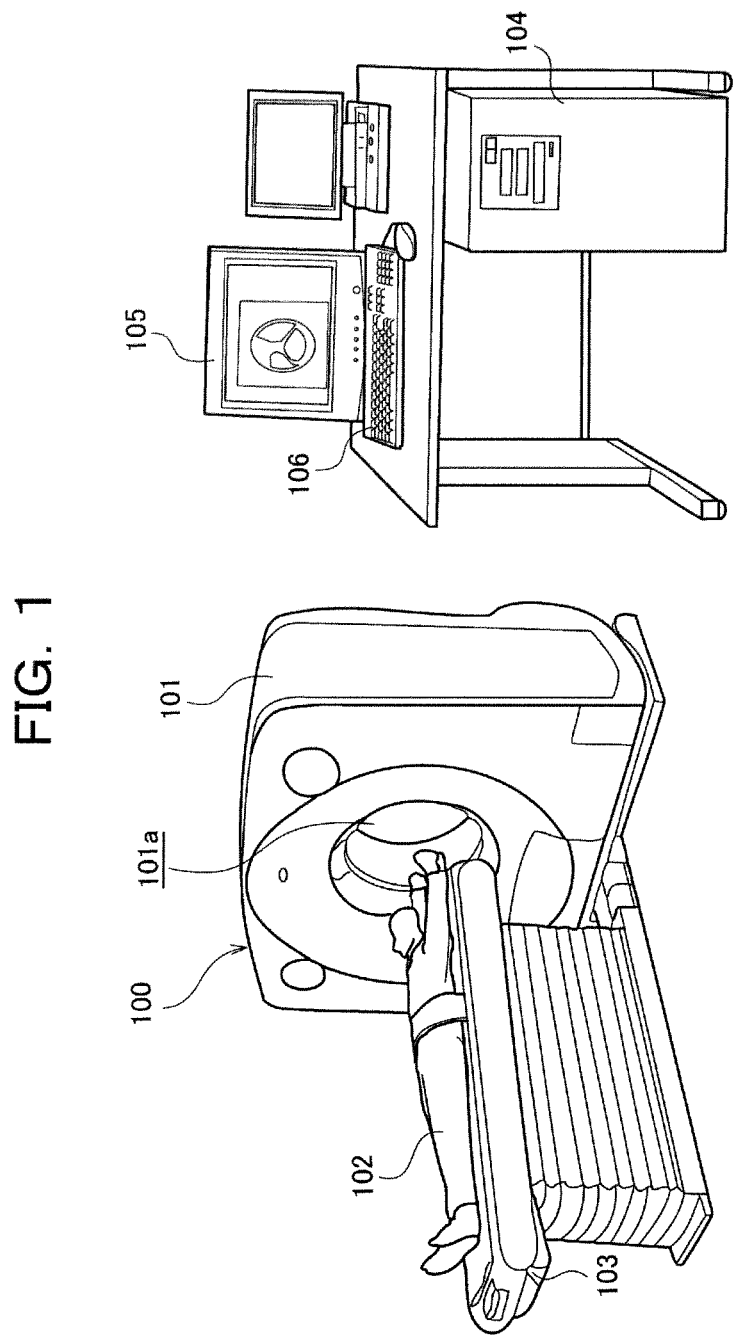
FIG. 1 is a schematic view showing an X-ray CT apparatus which uses a bed for a medical image scanning apparatus according to the present invention.

Overall configuration of an X-ray CT device 100 will be described with reference to FIG. 1. FIG. 1 is an overall configuration view of the X-ray CT apparatus. The X-ray CT apparatus 100 of FIG. 1 includes a gantry 101 on which an X-ray tube device or an X-ray detector is mounted and rotated around an object 102, and which detects the X-ray transmitting the object 102 and sends the transmitted X-ray signal; a bed 103 which disposes the object 102 on a top board and transports the object 102 to an opening 101a of the gantry 101; and a control device 104 which performs the X-ray photographing by controlling the X-ray CT apparatus 100 according to a photographing condition to which an operator inputs and includes an image processing portion which receives the transmitted X-ray signal sent from the gantry 101 and generates a reconstructed image; a display device 105 which displays the reconstructed image generated from the image processing portion; and an operating device 106 for inputting various commands to the control device 104. The bed 103 is a bed to which the present invention is applied, and the control device 104 controls the lifting and lowering movement or the lateral movement and the longitudinal movement of the bed 103, and the image processing or the inputting operation.

(Lifting and Lowering Device)

Figure 2:
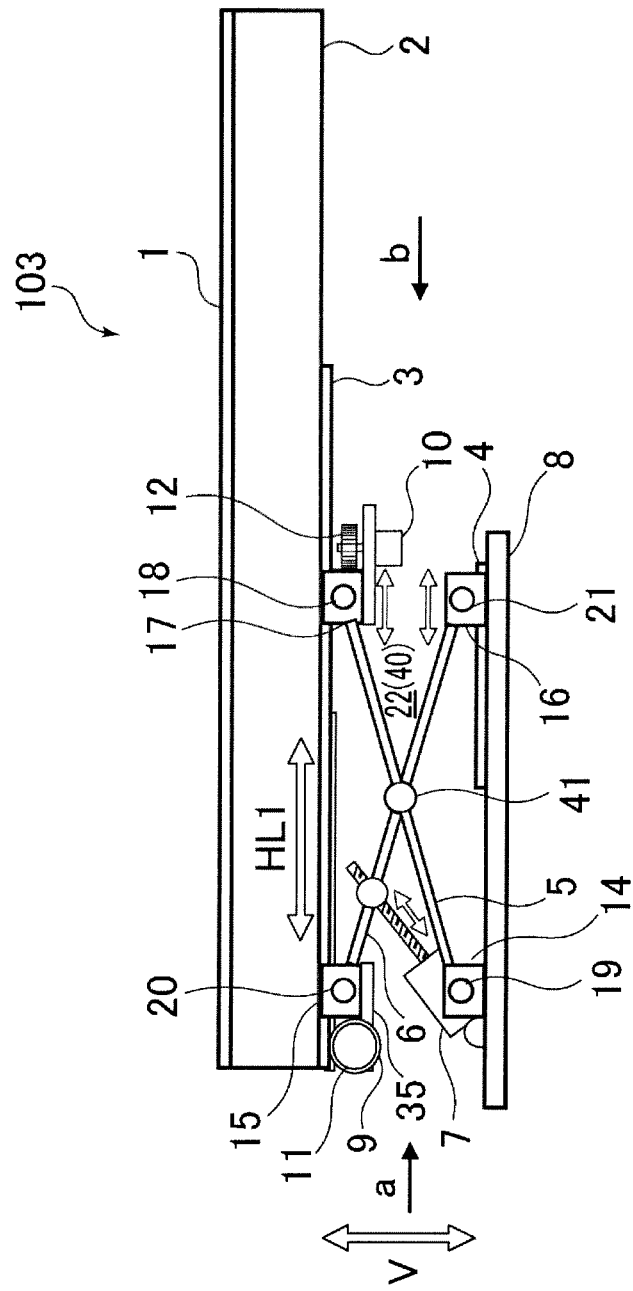
FIG. 2 is a front view showing the overall configuration of a bed for a medical image scanning apparatus according to a first embodiment.
Figure 3:
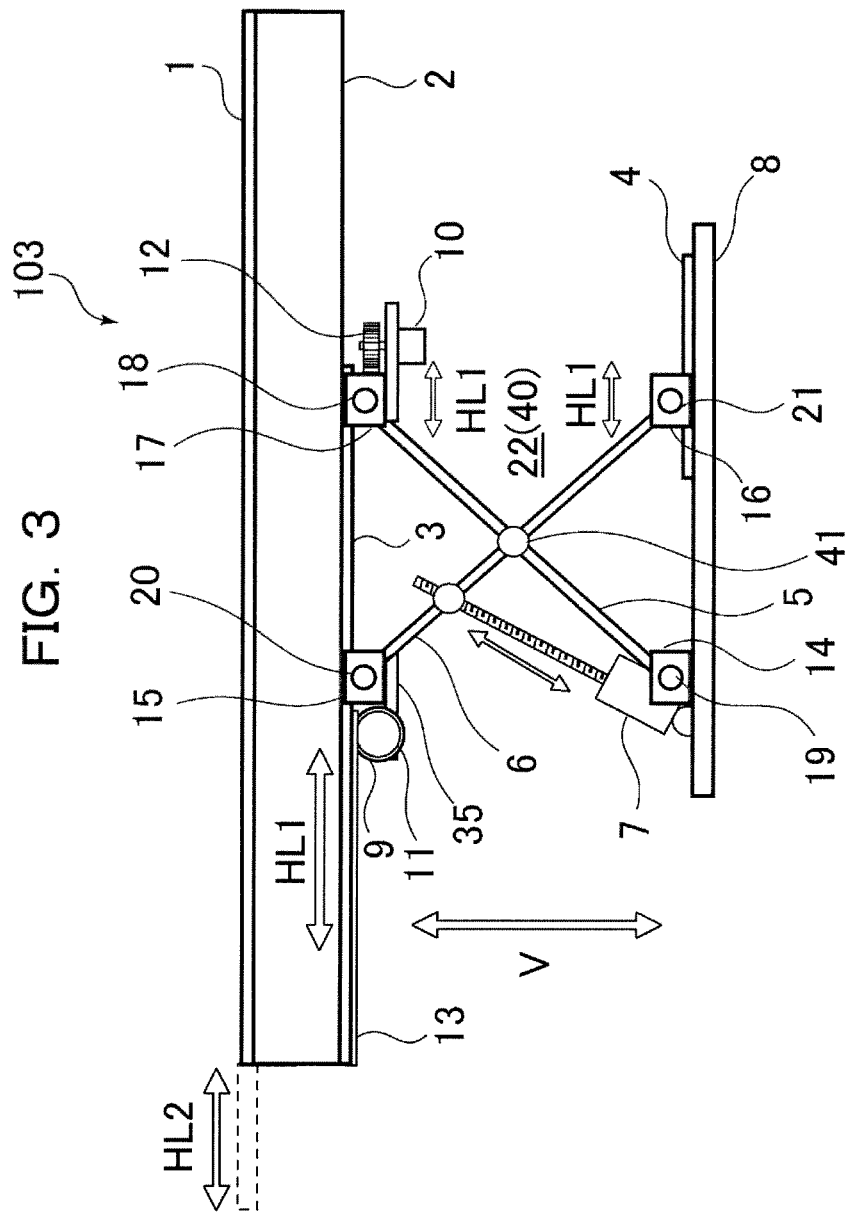
FIG. 3 is a front view showing a state where an upper portion frame is longitudinally moved and lifted in FIG. 2.
Figure 4:
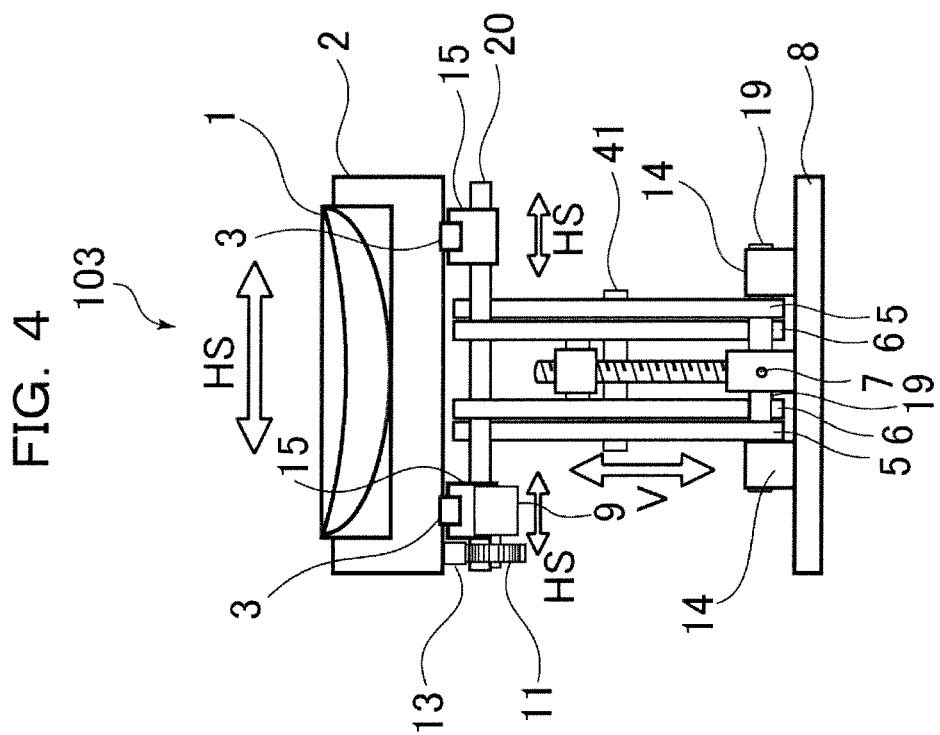
FIG. 4 is a side view showing a state when the upper portion frame is lowered when viewing the front view shown in FIG. 2 from an a direction.
Figure 5:
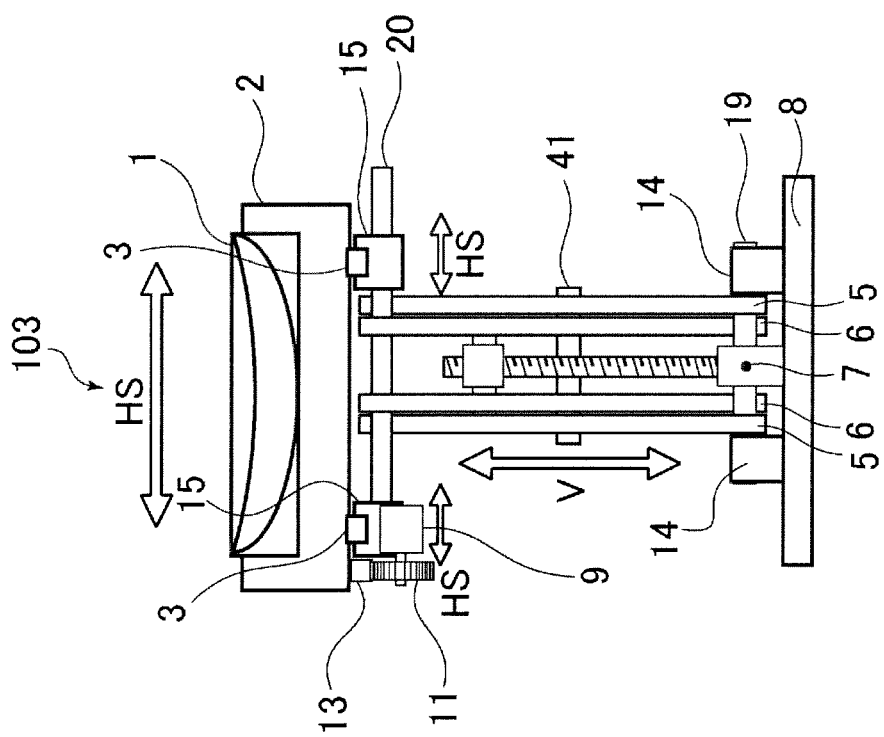
FIG. 5 is a side view showing a state where the upper portion frame is lifted in FIG. 4 and moved in the left direction when viewing the gantry at the front.

Next, the lifting and lowering device included in the bed 103 will be described with reference to FIGS. 2 to 5. FIG. 2 is a front view showing the overall configuration of the bed for the medical image bed apparatus according to the first embodiment. FIG. 3 is a front view showing a state where an upper portion frame is longitudinally moved and lifted in FIG. 2. FIG. 4 is a side view showing a state when the upper portion frame is lowered when viewing the front view shown in FIG. 2 from an a direction. FIG. 5 is a side view showing a state where the upper portion frame is lifted in FIG. 4 and moved in the left direction when viewing the gantry at the front.

The bed 103 includes a top board 1 which disposes an object, an upper portion frame 2 which includes a mechanism (not shown) moving the top board 1 in the lengthwise direction (hereinafter, referred to as a "longitudinal direction"), and a pantograph type of arm portion 22 which connects the upper portion frame 2 and the base 8.

The arm portion 22 is constituted so as to include two pantographic arms 40 and 40 between the upper portion frame 2 and the base 8 so that a widening and narrowing direction of each pantographic arm 40 and 40 is parallel to the longitudinal direction of the top board 1.

In each pantographic arm 40, an outer arm 5 is crossed to an inner arm 6 in an approximate X-shape, and the outer arm 5 and the inner arm 6 are rotatably connected with center pin 41 as the crossing point.

The upper end of the inner arm 6 is rotatably connected to a rail receiving block 15 of the upper portion frame 2 side by a rotation axis 20, and the lower end of the inner arm 6 is rotatably connected to a rail receiving block 16 of the base 8 side by a rotation axis 21. The upper end of the outer arm 5 is rotatably connected to a rail receiving block 17 of the upper portion frame 2 side by a rotation axis 18, and the lower end of the outer arm 5 is rotatably connected to a fixing block 14 which is fixed to the upper surface of the base 8 by a rotation axis 19. Since the center pin 41 and the rotation axes 18 to 21 are used in common in two pantographic arms 40 and 40, the two pantographic arms 40 and 40 are connected so as to be interlocked with each other. In addition, the rotation axes 18 to 21 may directly connect the upper portion frame and the rail receiving block, and may indirectly connect them via other members as described in a third embodiment below.

Two guide rails 3 and 3 are attached from the front portion of the lower surface of the upper portion frame 2 to the vicinity of each right end and left end of the center portion in the longitudinal direction of the upper portion frame 2 so that the longitudinal direction of the top board 1 and the axis directions of the guide rails 3 and 3 are parallel to each other. The rail receiving blocks 15 and 17 of each pantographic arm 40 are fitted to each guide rail 3, and these slide along the guide rail 3. In addition, two guide rails 4 and 4 may be provided in the vicinity of each right end and left end in the rear portion of the upper surface of the base 8. The rail receiving block 16 of each pantographic arm 40 is fitted to each guide rail 4 and slides along the guide rail 4.

A hydraulic cylinder 7 is rotatably fixed to the rotation axis 19 in the lower end of the outer arm 5. The driving shaft of the hydraulic cylinder 7 is connected to be pin-jointed to the inner arm 6. When the driving shaft of the hydraulic cylinder 7 is moved forward and backward, an included angle of the inner arm 6 and the outer arm 5 is widened and narrowed while interlocking therewith, the rail receiving blocks 15 and 17 slide along the guide rail 3, and the rail receiving block 16 slides along the guide rail 4. Thereby, the pantographic arms 40 and 40 are contracted and extended, and the lifting and lowering device in which the upper portion frame 2 is lifted and lowered (a direction of an arrow V) with respect to the base 8 is constituted.

(Longitudinal Movement Device)

A motor 9 is fixed to the rail receiving block 15 by a motor supporting frame 35. A pinion gear 11 may be provided to the driving shaft of the motor 9. In addition, a rack 13 engaged with the pinion gear 11 may be provided in the front side of the lower surface of the upper portion frame 2 along the guide rail 3. If the motor 9 is rotated, the pinion gear 11 and the rack 13 are engaged with each other, and a rotational movement of the pinion gear 11 is changed into a linear movement along the rack 13. In addition, the motor 9 and the rail receiving block 15 (and the rail receiving block 17 interlocking therewith) slide along the guide rail 3, and the upper portion frame 2 is relatively moved (a direction of an arrow HL1) with respect to the rail receiving block 15 and the rail receiving block 17 (and base 8). Thereby, the top board 1 disposed on the upper portion frame 2 is moved to a direction toward the opening 101a (hereinafter, referred to as a "longitudinal direction" in the present embodiment), and the longitudinal movement device is constituted.

(Lateral Movement Device)

Figure 6:
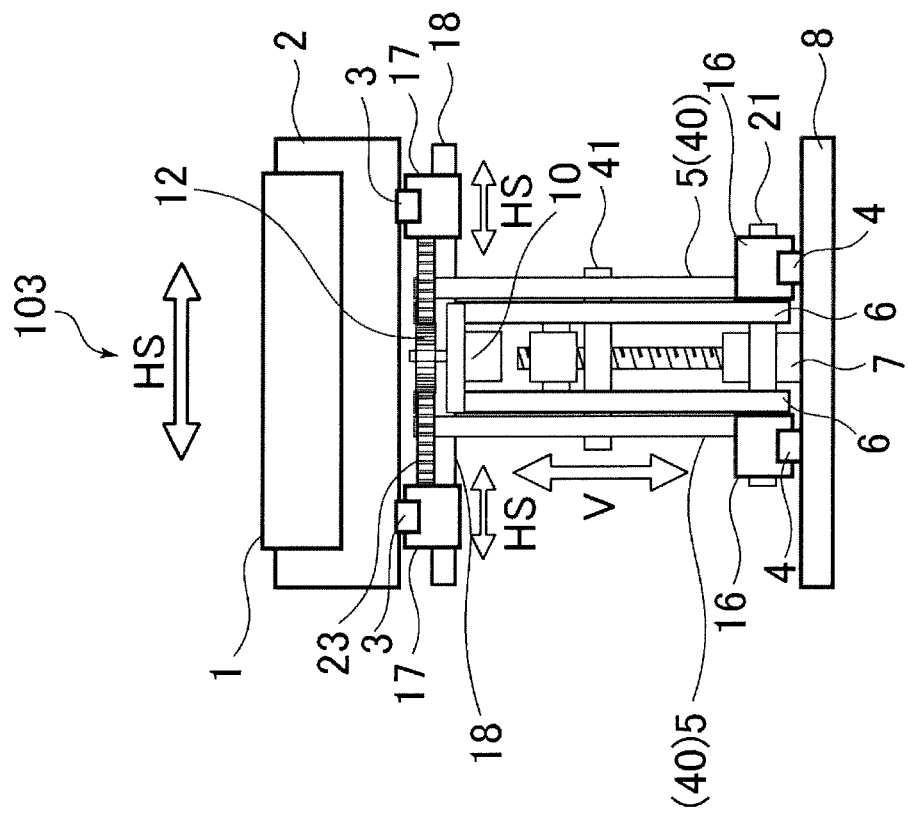
FIG. 6 is a side view showing a state when the upper portion frame is lowered when viewing the front view shown in FIG. 2 from a b direction.
Figure 7:
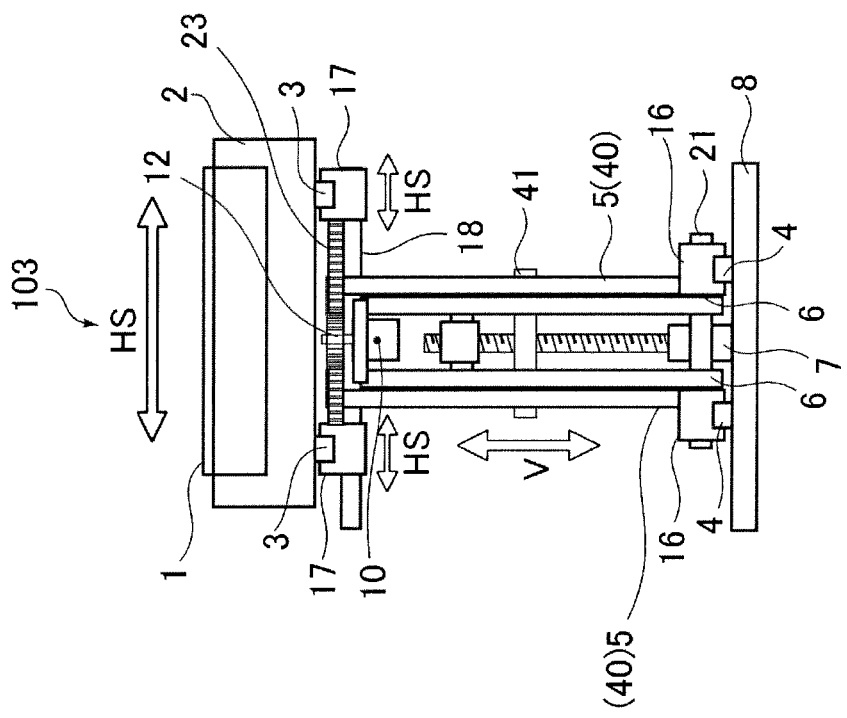
FIG. 7 is a side view showing a state where the upper portion frame is lifted in FIG. 6 and moved in the right direction when viewing the gantry at the front.
Figure 8:
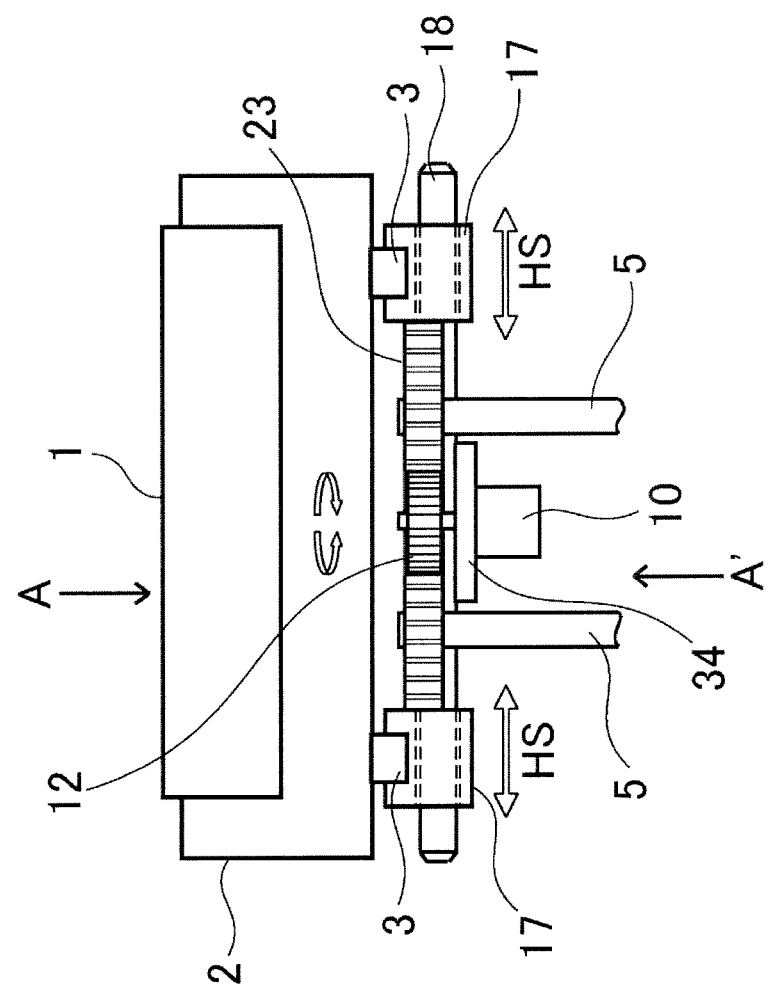
FIG. 8 is a partial enlarged view of a side view showing a main portion of a lateral movement device.
Figure 9:
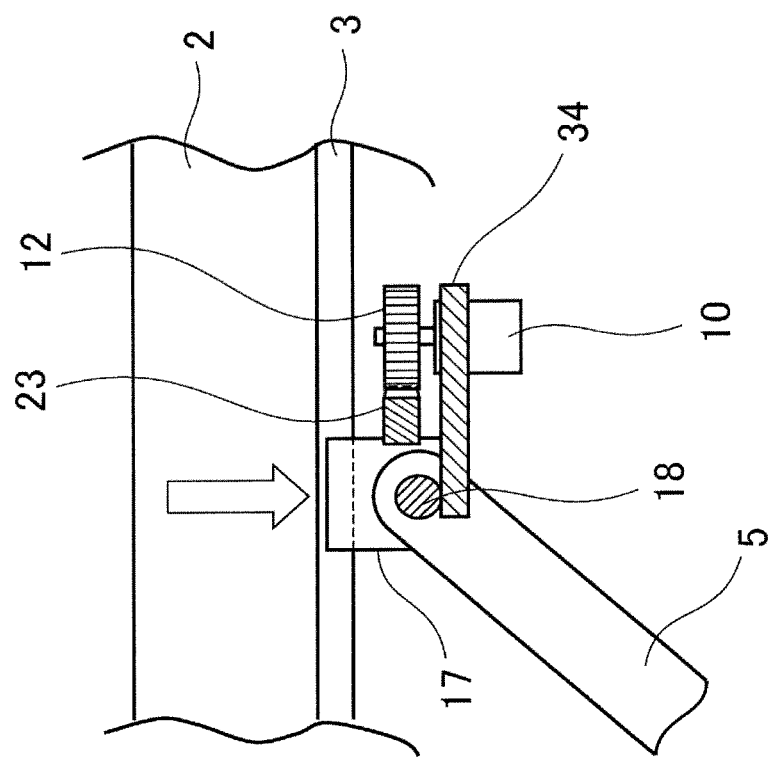
FIG. 9 is a cross-sectional enlarged view taken along a line A-A' of FIG. 8.

Next, a lateral movement device will be described with reference to FIGS. 6 to 9. FIG. 6 is a side view showing a state when the upper portion frame is lowered when viewing the front view shown in FIG. 2 from a b direction. FIG. 7 is a side view showing a state where the upper portion frame is lifted in a FIG. 6 and moved in the right direction when viewing the gantry at the front. FIG. 8 is a partial enlarged view of a side view showing a main portion of the lateral movement device. FIG. 9 is a cross-sectional enlarged view taken along a line A-A' of FIG. 8.

Rearward of the lower surface of the upper portion frame 2, a rack 23, which is used in common for a function as a supporting member connecting between the rail receiving blocks 17 of the left and right pantographic arms 40 and 40 and a function transmitting the driving force, is mounted along a direction (hereinafter, referred to as a "lateral direction") perpendicular with respect to the longitudinal direction of the upper portion frame 2 in the top board surface of the top board 1. In addition, a motor 10 is fixed to the rotation axis 18 by a motor supporting frame 34. The pinion gear 12 is connected to the driving shaft of the motor 10, and the pinion gear 12 is engaged with the rack 23.

If the pinion gear 12 is rotated by the motor 10, the rotational movement of the pinion gear 12 is changed to the linear movement along the rack 23, and the rack 23 and the rail receiving block 17 are relatively moved in the lateral movement (a direction of an arrow HS) with respect to the rotation axis 18. Thereby, the lateral movement device, which moves the top board 1 and the upper portion frame 2 in the left and the right directions with respect to the opening 101a, is constituted.

(Operation Explanation)

Next, the operation of the bed 103 according to the present embodiment will be described. The hydraulic cylinder 7, the motor 9, and the motor 10 are controlled according to a control signal from the control device 104, and therefore, the lifting and lowering device, the lateral movement device, and the longitudinal movement device perform each operation described below.

When the top board 1 is positioned from the lowest position to the height of the opening 101a of the gantry, the upper portion frame 2 performs the lifting movement and the longitudinal movement. When the upper portion frame 2 is lifted, the included angle between the inner arm 6 and the outer arm 5 is changed due to the fact that the hydraulic cylinder 7 is extended, the rail receiving block 16 of the inner arm 6 and the rail receiving block 17 of the outer arm 5 each slide to the gantry 101 side along the guide rails 3 and 4, and the upper portion frame 2 is lifted from the lowest level shown in FIGS. 2, 4, and 6 to the highest level shown in FIGS. 3, 5, and 7. When the upper portion frame is lowered, the rail receiving blocks 16 and 17 each slide to the reverse side (the direction which goes away from the gantry).

When the upper portion frame 2 advances (the movement which approaches the gantry), the pinion gear 11 is rotated due to the fact that the motor 9 is rotated, the pinion gear 11 delivers the rack 13 to the gantry side. According to this, the top board 1 and the upper portion frame 2 advance (the direction of the arrow HL1) with respect to the base 8 from the state of FIG. 2 to the state of FIG. 3 due to the fact that the rail receiving blocks 15 and 17 slide on the guide rail 3. When the upper portion frame recedes, the motor 9 is reversely rotated. After the top board 1 enters into the opening 101a of the gantry, the top board 1 is relatively and longitudinally moved (a direction of an arrow HL2) with respect to the upper portion frame 2 by a longitudinal movement device (not shown). In this time, the upper portion frame 2 is not longitudinally moved and performs only the lifting and lowering movement. That is, the rail receiving block 15 is fixed, and the rail receiving blocks 16 and 17 slide. Thereafter, in order to match a center of an effective photographing range and a center of a photographing region (for example, a center of heart) which is deviated from the body axis, the upper portion frame 2 is laterally moved.

When the upper portion frame is laterally moved, the pinion gear 12 is rotated due to the fact that the motor 10 attached to the rotation axis 18 is rotated. In addition, if the rack 23 is conveyed to the right as shown in FIG. 7, the upper portion frame 2 is laterally moved to the right direction along the rotation axis 18 according to the rail receiving block 17. When the upper portion frame is left moved, the motor 10 is reversely rotated.

In the bed 103 of the present embodiment, the guide rail 3 and the rail receiving blocks 15 and 17, and the guide rail 4 and the rail receiving block 16 are used in common for the longitudinal movement and the lifting and lowering movement, and the rail receiving blocks 15 and 17 are used in common for the lateral movement and the lifting and lowering movement. Moreover, the rail receiving blocks 15 and 17 and the rotation axis 20 and 18 are relatively moved in the lateral direction by using the driving mechanism constituted by the combination of the pinion gear and the rack. Thereby, in order to perform the longitudinal movement and the lateral movement of the upper portion frame 2, the bed 103 can be laterally moved without needing a multilayered structure. In addition, since the driving mechanism of the longitudinal movement and the driving mechanism of the lifting and lowering movement of the upper portion frame 2 are independent of each other while the parts are used in common, the position of the upper portion frame 2 can be freely set, and the operation space between the bed 103 and the gantry 101 can be secured while keeping the effective photographing range of the bed in the related art.

Moreover, in the bed 103 of the present embodiment, the rail receiving block 17 (and 15) receives the load from the upper portion frame 2 as shown in an arrow of FIG. 9. Then, since the distance between the rail receiving block 17 which is a portion receiving the load and the lateral movement device (the generic term of the motor 10, the pinion gear 12, the rack 23, the rotation axis 18, the rail receiving block 17, and the motor supporting frame 34) is shorter compared to the case where the lateral movement device is disposed in the vicinity of the base 8, deformation (distortion) according to the lateral movement is decreased, and the operation of the lateral movement can be more stably performed.

According to the bed for a medical image scanning apparatus of the present embodiment described above, the object disposed on the top board can be laterally moved, and an X-ray irradiation toward a non-photographing region can be decreased when a specific region such as heart is photographed. In addition, since height of the bed is low in the lowest position, operation for lifting and lowering infants or movement-impaired objects can be easily performed. Moreover, the number of parts used in the bed is greatly decreased, the bed becomes light, and deformation of moving portions and the intermediate supporting members can be decreased.

In addition, in the bed according to the present embodiment, since the longitudinal movement device which longitudinally moves the upper portion frame with respect to the base and the longitudinal movement device (not shown) which moves the top board with respect to the upper portion frame are provided, the lateral movement device can be added without changing the height of the lowest level of the top board while the gap between the gantry and the bed is more widely secured. Thereby, since the operation space between the bed and the gantry can be sufficiently secured, a headrest of the object can easily installed on the top board, and an X-ray illumination device of a C-type arm can be easily installed between the bed and the gantry.

In the embodiment, the hydraulic cylinder 7 is used as the driving source of the lifting and lowering device. However, an electric cylinder may be used instead of the hydraulic cylinder 7. Moreover, instead of the combination of the pinion gear and the rack, other driving mechanisms, for example, a slide bush may be used.

In addition, in the embodiment, the case where two pantographic arms 40 and 40 are provided is described. However, the pantographic arm is not limited to two, and single pantographic arm may be used. In this case, single pantographic arm is connected to each rotation axis, and the rotation axis may be supported by the left and the right rail receiving blocks.

In addition, in the first embodiment, the lateral movement device and the longitudinal movement device are provided in the lifting and lowering device. However, the lateral movement of the top board can be performed even in a case when only the lateral movement device is provided in the lifting and lowering device. In this case, since the longitudinal movement device is not needed, the length of the guide rail 3 is shorter than that of the first embodiment (the guide rail is provided only in the front from the center of the longitudinal direction), and the upper end of the outer arm 5 is rotatably connected to the fixing block, which is fixed to the lower surface of the upper portion frame 2 instead of the rail receiving block 17, via the rotation axis 18. Moreover, the motor 9, the pinion gear 11, and the rack 13 are not provided in the above case. In addition, the rotation axis 18 and the fixing block may be relatively moved in the lateral direction by using the lateral movement device of the first embodiment. Therefore, the bed in which only the lateral movement device is provided in the lifting and lowering device can be constituted.

<<Second Embodiment>>

Figure 10:
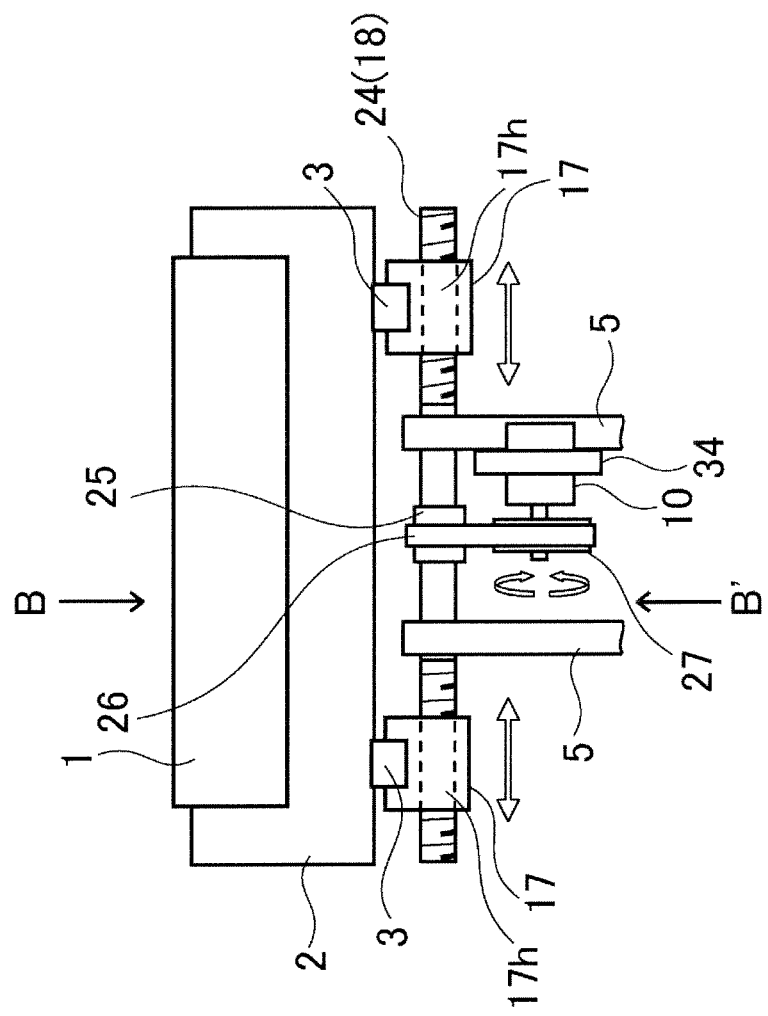
FIG. 10 is a side view showing a lateral movement device according to a second embodiment.
Figure 11:
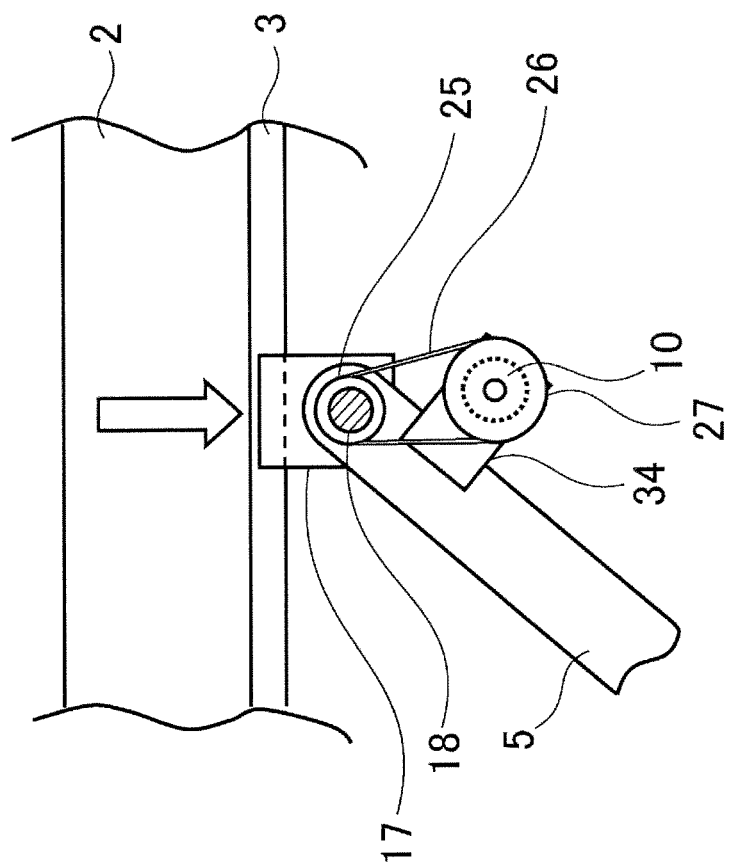
FIG. 11 is a cross-sectional enlarged view taken along a B-B' line of FIG. 10.

A second embodiment is a lateral movement device according to one alternative example of the lateral movement device of the first embodiment. Hereinafter, the lateral movement device according to the second embodiment will be described with reference to FIGS. 10 and 11. FIG. 10 is a side view showing a lateral movement device according to the second embodiment, and FIG. 11 is a cross-sectional enlarged view taken along a line B-B' of FIG. 10.

In the lateral movement device of the second embodiment, the upper portion frame 2 is laterally moved by using a ball screw 24 which is used as both the slide axis and the driving axis in the rotation axis 18. More specifically, each rail receiving block 17 includes a through hole 17h in which the rotation axis 18 penetrates and can be supported, and screw grooves (not shown) engaged to the ball screw 24 are provided in the inner peripheral surface of the hole.

On the other hand, the motor 10 is fixed to the vicinity of the upper end of the outer arm 5 by the motor supporting frame 34. A driving side pulley 27 is connected to the driving shaft of the motor 10. Also, a shaft side pulley 25 is provided in the ball screw 24. The driving side pulley 27 and the shaft side pulley 25 are connected to each other by a timing belt 26. Moreover, due to the fact that the motor 10 is rotated, the driving side pulley 27 is rotated, and the rotational movement is transferred to the shaft side pulley 25 via the timing belt 26. In addition, if the shaft side pulley 25 is rotated, the shaft side pulley 25 and the ball screw 24 are integrated and rotated, the ball screw 24 and the rail receiving blocks 17 and 17 are relatively moved along the axis direction (lateral direction) of the ball screw 24. Thereby, the upper portion frame 2 is integrated with the rail receiving block 17 and moved in the lateral direction.

<<Third Embodiment>>

Figure 12:
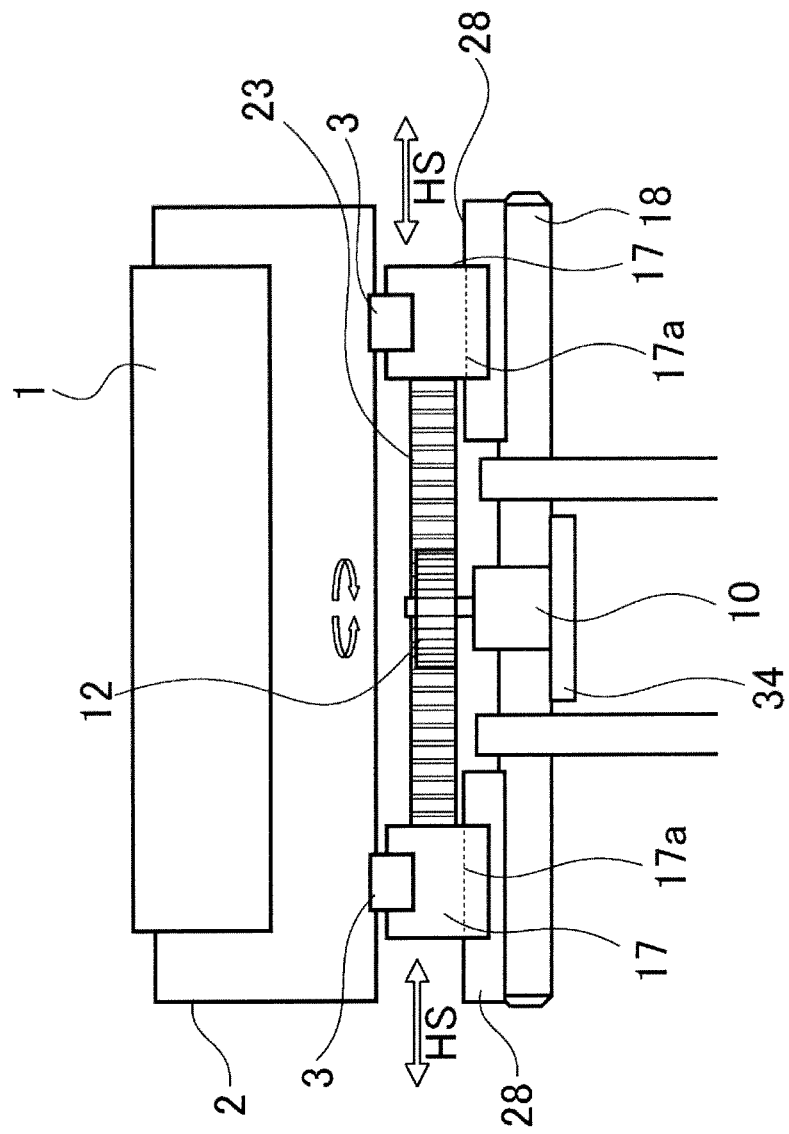
FIG. 12 is a partial enlarged view of a side view showing a lateral movement device according to a third embodiment.

Hereinafter, a lateral movement device according to a third embodiment will be described with reference to FIG. 12. FIG. 12 is a partial enlarged view of a side view showing the lateral movement device according to the third embodiment. The lateral movement device according to the third embodiment is a lateral movement device which connects the rotation axis 18 of the pantographic arm 40 and the rail receiving block 17 which is provided in the lower surface of the upper portion frame 2 via the guide rail 28 along the lateral direction. In the lateral movement device, the rotation axis 18 constituting the lifting and the lowering device and the rail receiving block 17 constituting the lifting and lowering device and the longitudinal movement device are used in common as parts of the lateral movement device. In the first and second embodiments, the rail receiving block functions as the rotation bearing. However, in the third embodiment, the rail receiving block does not function as the rotation bearing, instead, the outer frame 5 is rotated with respect to the rotation axis 18. In addition, in the first and second embodiments, the rotation axis 18 and the rail receiving block 17 are directly connected to each other. However, in the present embodiment, the rotation axis 18 and the rail receiving block 17 are indirectly connected to each other via a guide rail of the lateral direction described below.

As shown in FIG. 12, the lateral movement device according to the third embodiment includes the guide rail 28 on the upper surface of each left end and right end of the rotation axis 18, and rail grooves 17a and 17a are provided along the lateral direction in the lower end of each rail receiving block 17 and 17. Due to the fact that the guide rail 28 travels along the rail grooves 17a and 17a, the rail receiving block 17 and the rotation axis 18 are relatively moved in the lateral direction. In addition, in the lateral movement device according to the present embodiment, the rack 23 which connects the left and the right rail receiving blocks 17 and 17 is provided.

The motor 10 is fixed to the approximate center portion in the axis direction of the rotation axis 18 by the motor supporting frame 34. The pinion gear 12 is connected to the driving shaft of the motor 10, and the pinion gear 12 is engaged with the rack 23.

If the motor 10 is rotated, the pinion gear 12 is rotated by the driving of the motor 10. The rack 23 is carried in the lateral direction according to the rotation of the pinion gear 12. In addition, the rail receiving blocks 17 and 17 and the upper portion frame 2 are integrated with the rack 23 and moved in the lateral direction.

<<Fourth Embodiment>>

A fourth embodiment is a lateral movement device corresponding to other aspect of the lateral movement device using the guide rail. In the lateral movement device of the fourth embodiment, the guide rail and the rail receiving block of the third embodiment (FIG. 12) are disposed to be upside down. Moreover, in the first and second embodiments, the rotation axis 18 and the rail receiving block 17 are directly connected to each other. However, in the present embodiment, the rotation axis 18 and the rail receiving block 17 are indirectly connected to each other via a guide rail of the lateral direction, a rail receiving block of the lateral direction, and the supporting block which are described below.

Figure 13:
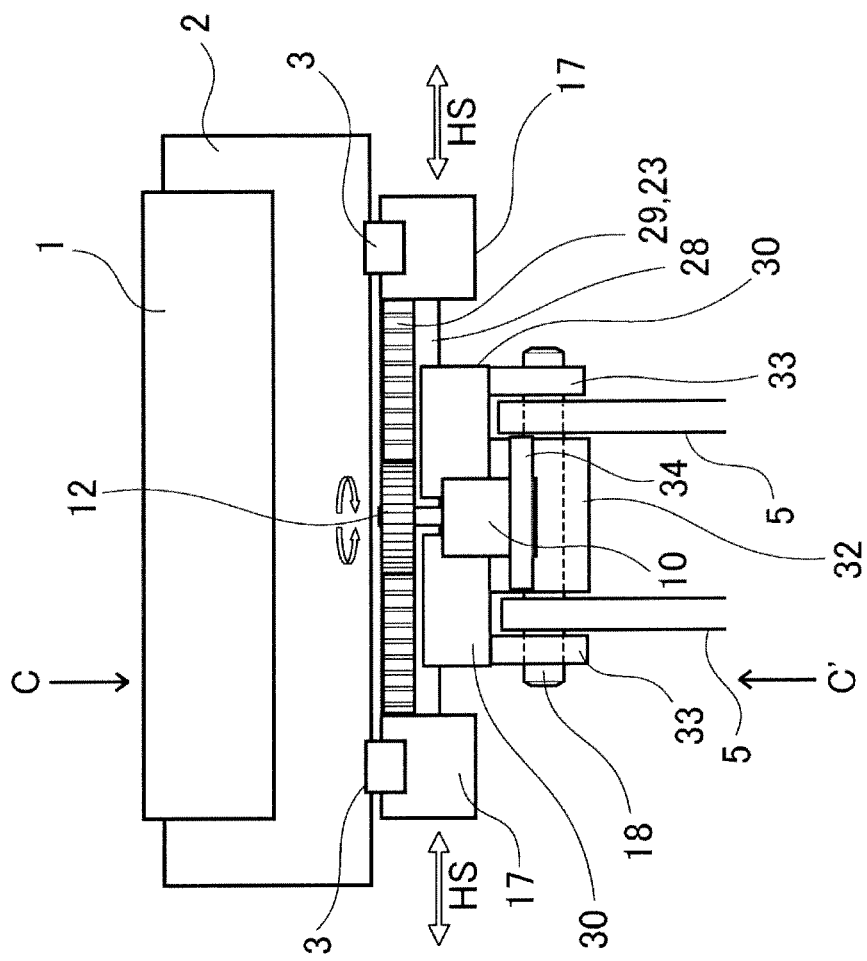
FIG. 13 is a partial enlarged view of a side view showing a lateral movement device according to a fourth embodiment.

Next, the lateral movement device according to the fourth embodiment will be described with reference to FIGS. 13 and 14. FIG. 13 is a partial enlarged view of a side view showing the lateral movement device according to the fourth embodiment, and FIG. 14 is a partial cross-sectional enlarged view taken along a line C-C' of FIG. 13.

In the lateral movement device according to the present embodiment, the guide rail 28 for the lateral movement is fixed with respect to the supporting frame 29 which connects the left and right rail receiving blocks 17. The rail receiving block 30 attached to the guide rail 28 is fixed to the rotation axis 18 via the supporting blocks 32 and 33. In addition, the rack 23 is fixed to the supporting frame 29 along the longitudinal direction of the supporting frame. The motor 10 is fixed to the supporting block 32, which penetrates and supports the rotation axis 18, by the motor supporting frame 34. The pinion gear 12 is connected to the driving shaft of the motor 10, and the pinion gear 12 is engaged with the rack 23. If the motor 10 is rotated, the pinion gear 12 is rotated, the rack 23 is carried, and the supporting frame 29 is carried while interlocking therewith. At this time, the rail receiving block 30 is moved along the guide rail 28. Thereby, the supporting frame 29 and the rail receiving block 17, and the supporting frames 32 and 33 and the rotation axis 18 are relatively moved in the lateral direction. As a result, the upper portion frame 2 is laterally moved.

Figure 14:
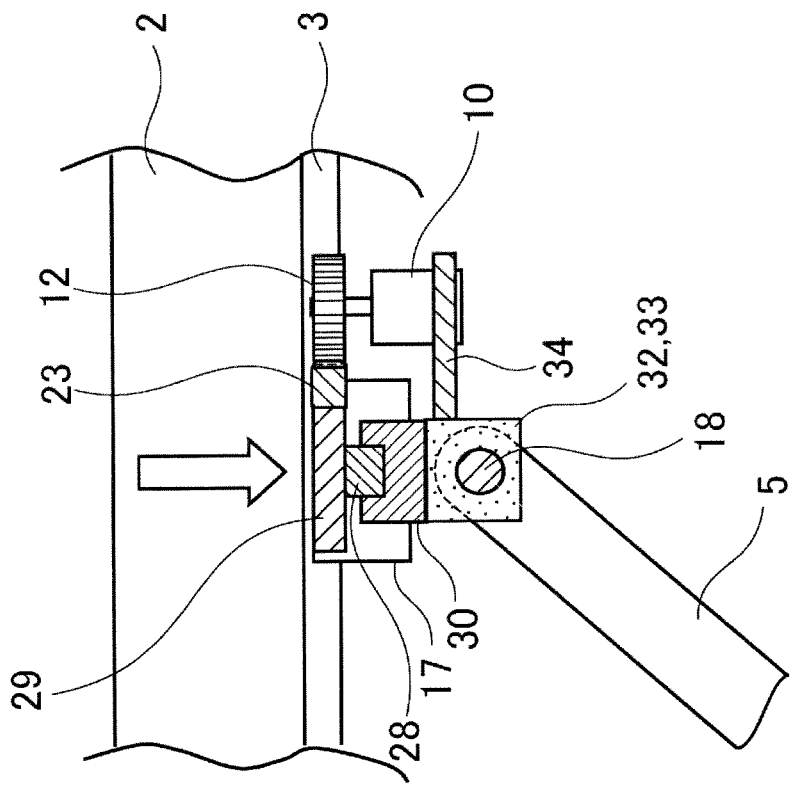
FIG. 14 is a partial cross-sectional enlarged view taken along a line C-C' of FIG. 13

As shown in a cross-sectional view of FIG. 14, the load of the upper portion frame 2 shown as an arrow in FIG. 14 is transferred to the guide rail 28 and the rail receiving block 30 disposed just below thereof via the guide rail 3, the rail receiving block 17, and the supporting arm 29, and the load is directly transferred to the rotation axis 18 via the supporting blocks 32 and 33.

Due to the fact that the lateral movement devices are constituted in this way, the lateral movement device can be constituted by a minimum of required members, the supporting structure is solid, and accuracy of the driving mechanism is improved due to fact that deformation of the supporting structural portion is decreased. In addition, since the position relationship of the load supporting portions is constantly maintained regardless of the positions of the lifting and lowering movement and the longitudinal movement, load can be directly transferred to the just below structural portions at all times without going through the intermediate frame-like supporting structures in which the load operating positions are different such as the multistep structure in the related art. Therefore, deformation of the supporting structural portions according to the lifting and lowering movement and the longitudinal movement can be considerably decreased.

Moreover, since the length of the rotation axis 18 can be shorter compared to each embodiment described above, the width of the structure of the lower portion (the fixing side) of the lateral movement device can be narrower, and the device can be miniaturized.

Figure 15:
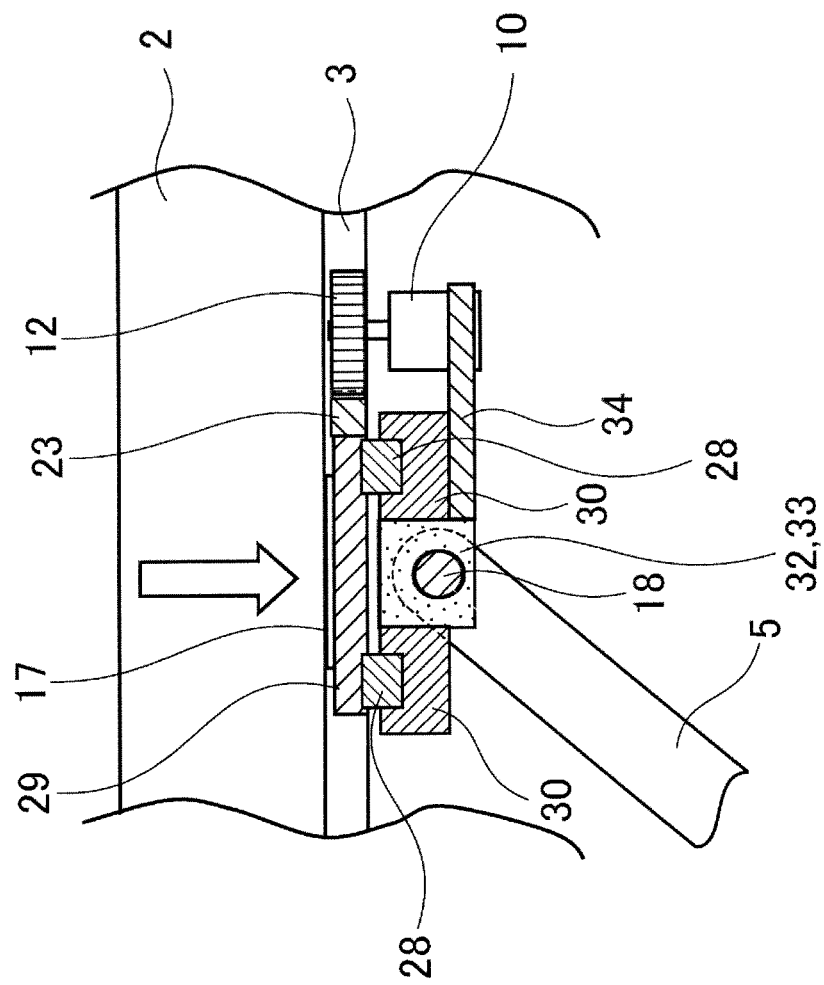
FIG. 15 is a partial cross-sectional enlarged view of a front view showing an alternative example of the mechanism shown in FIG. 14.

Next, an alternative example to the mechanism shown in FIG. 14 will be described with reference to FIG. 15. FIG. 15 is a partial cross-sectional enlarged view of a front view showing the alternative example of the mechanism shown in FIG. 14. In the case where the guide rail 28 and the rail receiving block 30 as shown in FIGS. 13 and 14 are used, the height of the mechanism becomes slightly greater. However, as shown in FIG. 15, due to methods in which two guide rails 28 and 28 of the front and back in the rotation axis 18 and the rail receiving block 30 are disposed in parallel and the like, the height of the mechanism can be decreased. Due to the fact that the upper load can be supported so as to be evenly distributed by disposing two guide rails 28 and 28 and the rail receiving blocks 30 and 30 in parallel, the load of the upper portion frame 2 can be directly supported similarly to FIG. 14 while decreasing the height of the mechanism.

According to the embodiments, in the bed for the medical image scanning apparatus of the related art having the lifting and the lowering device and the longitudinal movement device, the lateral movement device can be added without changing the height of the lowest level, and the object can be moved in the lateral direction in the state where the object is disposed on the top board 1.

In addition, since components of the lifting and lowering device or the longitudinal movement device and components of lateral movement device are used in common, when the lateral movement device is compared to that of the multistep structure (the structure in which the thickness of the lateral movement device is added to the height of the lifting and lowering device and the longitudinal movement device), the number of parts can be considerably deceased, the lateral movement device becomes light weight, amount of deformation in operating portions or intermediate supporting members can be decreased.

In each embodiment, the lateral movement device is provided in the rear portion of the upper portion frame 2. However, the lateral movement device may be provided in the front side of the upper portion frame 2, that is, the rail receiving block 15 and the rotation axis 20. In addition, in each embodiment, single lateral movement device is provided in anyone of the front side or the rear side of the upper portion frame. However, a total of two lateral movement devices may each be provided in the front side and the rear side respectively, and a control device which interlocks the two lateral movement devices may be provided.

In addition, in each embodiment, the pantographic arm is used as the arm portion 22. However, instead of the pantographic arm, the above-described embodiments each may be also applied to a cobra arm type of bed, in which the upper portion frame 2 is lifted while being longitudinally moved due to the fact that the arm is moved in parallel about a fixing block which is fixed to the base and rotated. Since the cobra arm is a device which longitudinally moves the upper portion frame 2 by the rotation angle of the arm, by applying the present invention to the cobra arm, the longitudinal movement device can include the lateral movement device.

In addition, in each embodiment, the rail receiving block and the rotation axis are relatively moved by using the lateral movement device. However, the lateral movement can be performed even when the upper portion connecting member including the rail receiving block and the rotation axis, and the pantographic arm or the arm portion of the cobra arm are relatively moved.

DESCRIPTION OF REFERENCE NUMERALS

1: TOP BOARD, 2: UPPER PORTION FRAME, 3: GUIDE RAIL, 4: GUIDE RAIL, 5: OUTER ARM, 6: INNER ARM, 7: HYDRAULIC CYLINDER, 8: BASE, 9: MOTOR, 10: MOTOR, 11: PINION GEAR, 12: PINION GEAR, 13: RACK, 14: FIXING BLOCK, 15: RAIL RECEIVING BLOCK, 16: RAIL RECEIVING BLOCK, 17: RAIL RECEIVING BLOCK, 17a: RAIL GROOVE, 17h: THROUGH HOLE, 18: ROTATION AXIS, 19: ROTATION AXIS, 20: ROTATION AXIS, 21: ROTATION AXIS, 22: ARM PORTION, 23: RACK, 24: BALL SCREW, 25: SHAFT SIDE PULLEY, 26: TIMING BELT, 27: DRIVING SIDE PULLEY, 28: GUIDE RAIL, 29: SUPPORTING FRAME, 30: RAIL RECEIVING BLOCK, 32: SUPPORTING BLOCK, 33: SUPPORTING BLOCK, 34: MOTOR SUPPORTING FRAME, 40: PANTOGRAPHIC ARM, 41: CENTER PIN, 100: X-RAY CT APPARATUS, 101: GANTRY, 101a: OPENING, 102: OBJECT, 103: BED, 104: IMAGING PROCESSING DEVICE, 105: DISPLAY DEVICE, 106: OPERATING DEVICE

The invention claimed is:

1. A bed for a medical image scanning apparatus comprising:
    a base;
    an upper portion frame that supports a top board; and
    a lifting and lowering device that is positioned between the base and the upper portion frame and lifts and lowers the upper portion frame,
    wherein the lifting and lowering device includes:
        an arm portion to change height in a vertical direction with respect to the base;
        an upper connecting portion that connects an upper end of the arm portion to the upper portion frame, and includes a guide rail that is fixed to a lower surface of the upper portion frame and regulates a movement along a longitudinal direction of the upper portion frame, a rail receiving block that moves in the longitudinal direction along the guide rail, and a rotation axis that penetrates the rail receiving block and an upper end of the arm portion; and
        a lateral movement device which relatively moves the rail receiving block and the rotation axis along a lateral direction which is a direction perpendicular to the longitudinal direction in the top board surface of the top board.

2. The bed for a medical image scanning apparatus according to claim 1,
    wherein the lateral movement device is provided on an upper end of the lifting and lowering device.

3. The bed for a medical image scanning apparatus according to claim 2,
    wherein the lifting and lowering device includes:
    a lower connecting portion that connects a lower end of the arm portion to the base,
    wherein the lateral movement device includes a driving mechanism which relatively moves at least two members constituting the upper connecting portion along the lateral direction or relatively moves the upper connecting portion and the arm portion along the lateral direction.

4. The bed for a medical image scanning apparatus according to claim 3,
    wherein
    the driving mechanism of the lateral movement device relatively moves the rail receiving block and the rotation axis along the lateral direction.

5. The bed for a medical image scanning apparatus according to claim 4,
    wherein the guide rails is one of at least two guide rails of the upper connecting portion, and the rail receiving block is one of at least two rail receiving blocks in a lower surface of the upper portion frame, and
    the driving mechanism includes a lateral direction rack that connects the at least two rail receiving blocks, a lateral driving device that is fixed to the rotation axis, and a first pinion gear that is connected to a driving shaft of the lateral driving device and rotated and engaged with the lateral direction rack.

6. The bed for a medical image scanning apparatus according to claim 4,
    wherein the guide rails is one of at least two guide rails of the upper connecting portion, and the rail receiving block is one of at least two rail receiving blocks in a lower surface of the upper portion frame,
    a through hole for inserting the rotation axis is provided in each rail receiving block, and
    the driving mechanism includes a ball screw that constitutes the rotation axis, a screw groove that is provided in an inner surface of the through hole and is screwed to the ball screw, a lateral driving device that is fixed to the arm portion, a first pulley that is connected to a driving shaft of the lateral driving device, a second pulley that is provided in the ball screw and, a timing belt that connects the first pulley and the second pulley and transfers a driving force of the lateral driving device.

7. The bed for a medical image scanning apparatus according to claim 4,
    wherein the guide rails is one of at least two guide rails of the upper connecting portion, and the rail receiving block is one of at least two rail receiving blocks in a lower surface of the upper portion frame,
    the lateral movement device includes a lateral-direction guide rail that regulates a movement along the lateral direction of the rail receiving block between the rotation axis and the rail receiving block, and
    the driving mechanism includes a lateral direction rack that connects at least two rail receiving blocks, a lateral driving device that is fixed to the rotation axis, and a first pinion gear that is rotatably connected to a driving shaft of the lateral driving device and engaged with the lateral direction rack.

8. The bed for a medical image scanning apparatus according to claim 4,
    wherein the guide rails is one of at least two guide rails of the upper connecting portion, and the rail receiving block is one of at least two rail receiving blocks in a lower surface of the upper portion frame,
    the lateral movement device includes a supporting member that connects the at least two rail receiving blocks, and a lateral direction guide rail that is included in the supporting member and regulates a movement along the lateral direction, and
    the driving mechanism includes a lateral direction rack that is included in the supporting member along the lateral direction, a lateral direction rail receiving block that is fixed to the rotation axis and moved along the lateral direction guide rail, a lateral driving device that is fixed to the lateral direction rail receiving block, and a first pinion gear that is connected to a driving shaft of the lateral driving device and engaged with the lateral direction rack.

9. The bed for a medical image scanning apparatus according to claim 1,
wherein the lifting and lowering device further includes a longitudinal movement device that relatively moves the upper portion frame along a longitudinal direction of the upper portion frame with respect to the base.

10. The bed for a medical image scanning apparatus according to claim 4,
wherein the arm portion is a pantographic arm that crosses a first arm and a second arm in an approximate X-shape, rotatably connects the first arm and the second arm with the crossed portion as a center pin, and widens and narrows the first arm and the second arm along the longitudinal direction,
the rail receiving block is one of two rail receiving blocks that move along the guide rail, and the rotation axis is one of two rotation axes that connect each rail receiving block and an upper end of the first arm and an upper end of the second arm, and
the lifting and lowering device further includes a longitudinal movement device that relatively moves the upper portion frame along a longitudinal direction of the upper portion frame with respect to the base, and the longitudinal movement device includes a longitudinal direction rack that is included in the guide rail along the longitudinal direction, a longitudinal driving device that is included in one of two rail receiving blocks, and a second pinion gear that is rotatably connected to a driving shaft of the longitudinal driving device and engaged with the longitudinal direction rack.

11. A bed for a medical image scanning apparatus comprising:
a base;
an upper portion frame that supports a top board; and
a longitudinal movement device that is positioned between the base and the upper portion frame and moves the upper portion frame along a longitudinal direction of the upper portion frame,
wherein the longitudinal movement device includes
a guide rail that is fixed to a lower surface of the upper portion frame and regulates a movement along a longitudinal direction of the upper portion frame;
a rail receiving block that moves in the longitudinal direction along the guide rail;
a rotation axis that penetrates the rail receiving block; and
a lateral movement device which relatively moves the rail receiving block and the rotation axis along a lateral direction which is a direction perpendicular to the longitudinal direction in the top board surface of the top board.

* * * * *